(12) United States Patent
Schaller et al.

(10) Patent No.: US 8,366,773 B2
(45) Date of Patent: Feb. 5, 2013

(54) APPARATUS AND METHOD FOR TREATING BONE

(75) Inventors: Laurent Schaller, Los Altos, CA (US); Steven Golden, Menlo Park, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 1213 days.

(21) Appl. No.: 12/020,396

(22) Filed: Jan. 25, 2008

(65) Prior Publication Data

US 2008/0154272 A1    Jun. 26, 2008

Related U.S. Application Data

(63) Continuation-in-part of application No. 11/464,782, filed on Aug. 15, 2006, now Pat. No. 7,785,368, and a continuation-in-part of application No. 11/464,790, filed on Aug. 15, 2006, now Pat. No. 7,666,226, and a continuation-in-part of application No. 11/464,793, (Continued)

(51) Int. Cl.
*A61F 2/44* (2006.01)
*A61B 17/88* (2006.01)

(52) U.S. Cl. .................................. 623/17.11; 606/279

(58) Field of Classification Search .......... 606/90, 606/279; 623/17.11–17.16

See application file for complete search history.

(56) References Cited

U.S. PATENT DOCUMENTS

| | | |
|---|---|---|
| 1,965,653 A | 7/1934 | Kennedy |
| 3,091,237 A | 5/1963 | Skinner |
| 3,112,743 A | 12/1963 | Cochran et al. |
| 3,648,294 A | 3/1972 | Shahrestani |
| 3,800,788 A | 4/1974 | White |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 4,262,676 A | 4/1981 | Jamshidi |
| 4,274,163 A | 6/1981 | Malcom et al. |
| 4,312,337 A | 1/1982 | Donohue |
| 4,313,434 A | 2/1982 | Segal |
| 4,399,814 A | 8/1983 | Pratt, Jr. et al. |
| 4,462,394 A | 7/1984 | Jacobs |
| 4,466,435 A | 8/1984 | Murray |

(Continued)

FOREIGN PATENT DOCUMENTS

| | | |
|---|---|---|
| DE | 197 10 392 C1 * | 7/1999 |
| DE | 19710392 C1 | 7/1999 |

(Continued)

OTHER PUBLICATIONS

USPTO Notice of Allowance and Fee(s) Due of Dec. 23, 2009 for U.S. Appl. No. 11/464,790.

(Continued)

*Primary Examiner* — Eduardo C Robert
*Assistant Examiner* — Julianna N Harvey
(74) *Attorney, Agent, or Firm* — Cook Alex Ltd.

(57) ABSTRACT

A bone tamp for creating channels within bone tissue. The bone tamp includes an elongated member that is deformable from a first generally non-linear configuration to a second generally linear configuration for insertion into bone tissue. As the elongated member is deployed into bone tissue, it transitions from the linear configuration into the non-linear configuration within the bone tissue. The elongated member is capable of being deformed back into the generally linear configuration for withdrawal from the bone tissue.

22 Claims, 3 Drawing Sheets

Related U.S. Application Data filed on Aug. 15, 2006, now Pat. No. 7,666,227, and a continuation-in-part of application No. 11/464,807, filed on Aug. 15, 2006, and a continuation-in-part of application No. 11/464,812, filed on Aug. 15, 2006, now Pat. No. 7,670,374, and a continuation-in-part of application No. 11/464,815, filed on Aug. 15, 2006, now Pat. No. 7,670,375.

(60) Provisional application No. 60/708,691, filed on Aug. 16, 2005, provisional application No. 60/738,432, filed on Nov. 21, 2005, provisional application No. 60/784,185, filed on Mar. 21, 2006, provisional application No. 60/886,838, filed on Jan. 26, 2007, provisional application No. 60/890,868, filed on Feb. 21, 2007, provisional application No. 60/936,974, filed on Jun. 22, 2007.

(56) References Cited

U.S. PATENT DOCUMENTS

| | | | |
|---|---|---|---|
| 4,467,479 | A | 8/1984 | Brody |
| 4,488,549 | A | 12/1984 | Lee et al. |
| 4,562,598 | A | 1/1986 | Kranz |
| 4,595,006 | A | 6/1986 | Burke et al. |
| 4,625,722 | A | 12/1986 | Murray |
| 4,627,434 | A | 12/1986 | Murray |
| 4,628,945 | A | 12/1986 | Johnson, Jr. |
| 4,630,616 | A | 12/1986 | Tretinyak |
| 4,665,906 | A | 5/1987 | Jervis |
| 4,686,973 | A | 8/1987 | Frisch |
| 4,697,584 | A | 10/1987 | Haynes |
| 4,706,670 | A | 11/1987 | Andersen et al. |
| 4,714,478 | A | 12/1987 | Fischer |
| 4,743,256 | A | 5/1988 | Brantigan |
| 4,772,287 | A | 9/1988 | Ray et al. |
| 4,834,069 | A | 5/1989 | Umeda |
| 4,838,282 | A | 6/1989 | Strasser et al. |
| 4,863,476 | A | 9/1989 | Shepperd |
| 4,878,915 | A | 11/1989 | Brantigan |
| 4,888,022 | A | 12/1989 | Huebsch |
| 4,888,024 | A | 12/1989 | Powlan |
| 4,892,550 | A | 1/1990 | Huebsch |
| 4,896,662 | A | 1/1990 | Noble |
| 4,898,577 | A | 2/1990 | Badger et al. |
| 4,904,261 | A | 2/1990 | Dove et al. |
| 4,941,466 | A | 7/1990 | Romano |
| 4,961,740 | A | 10/1990 | Ray et al. |
| 4,969,888 | A | 11/1990 | Scholten et al. |
| 5,015,247 | A | 5/1991 | Michelson |
| 5,015,255 | A | 5/1991 | Kuslich |
| 5,051,189 | A | 9/1991 | Farrah |
| 5,053,035 | A | 10/1991 | McLaren |
| 5,055,104 | A | 10/1991 | Ray |
| 5,059,193 | A | 10/1991 | Kuslich |
| 5,071,435 | A | 12/1991 | Fuchs et al. |
| 5,098,435 | A | 3/1992 | Stednitz et al. |
| 5,102,413 | A | 4/1992 | Poddar |
| 5,108,404 | A | 4/1992 | Scholten et al. |
| 5,122,130 | A | 6/1992 | Keller |
| 5,123,926 | A | 6/1992 | Pisharodi |
| 5,147,366 | A | 9/1992 | Arroyo et al. |
| 5,163,989 | A | 11/1992 | Campbell et al. |
| 5,171,280 | A | 12/1992 | Baumgartner |
| 5,176,683 | A | 1/1993 | Kimsey et al. |
| 5,176,692 | A | 1/1993 | Wilk et al. |
| 5,183,052 | A | 2/1993 | Terwilliger |
| 5,192,327 | A | 3/1993 | Brantigan |
| 5,228,441 | A | 7/1993 | Lundquist |
| 5,242,448 | A | 9/1993 | Pettine et al. |
| 5,242,879 | A | 9/1993 | Abe et al. |
| 5,257,632 | A | 11/1993 | Turkel et al. |
| 5,263,953 | A | 11/1993 | Bagby |
| 5,285,795 | A | 2/1994 | Ryan et al. |
| 5,303,718 | A | 4/1994 | Krajicek |
| 5,306,308 | A | 4/1994 | Gross et al. |
| 5,306,310 | A | 4/1994 | Siebels |
| 5,322,505 | A | 6/1994 | Krause et al. |
| 5,330,429 | A | 7/1994 | Noguchi et al. |
| 5,331,975 | A | 7/1994 | Bonutti |
| 5,361,752 | A | 11/1994 | Moll et al. |
| 5,383,932 | A | 1/1995 | Wilson et al. |
| 5,385,151 | A | 1/1995 | Scarfone et al. |
| 5,423,816 | A | 6/1995 | Lin |
| 5,423,817 | A | 6/1995 | Lin |
| 5,423,850 | A | 6/1995 | Berger |
| 5,431,658 | A | 7/1995 | Moskovich |
| 5,441,538 | A | 8/1995 | Bonutti |
| 5,454,365 | A | 10/1995 | Bonutti |
| 5,454,827 | A | 10/1995 | Aust et al. |
| 5,462,563 | A | 10/1995 | Shearer et al. |
| 5,468,245 | A | 11/1995 | Vargas, III |
| 5,480,400 | A | 1/1996 | Berger |
| 5,484,437 | A | 1/1996 | Michelson |
| 5,509,923 | A | 4/1996 | Middleman et al. |
| 5,514,143 | A | 5/1996 | Bonutti et al. |
| 5,514,153 | A | 5/1996 | Bonutti |
| 5,522,398 | A | 6/1996 | Goldenberg et al. |
| 5,522,790 | A | 6/1996 | Moll et al. |
| 5,522,846 | A | 6/1996 | Bonutti |
| 5,527,343 | A | 6/1996 | Bonutti |
| 5,527,624 | A | 6/1996 | Higgins et al. |
| 5,531,856 | A | 7/1996 | Moll et al. |
| 5,534,023 | A | 7/1996 | Henley |
| 5,538,009 | A | 7/1996 | Byrne et al. |
| 5,540,711 | A | 7/1996 | Kieturakis et al. |
| 5,545,222 | A | 8/1996 | Bonutti |
| 5,549,679 | A | 8/1996 | Kuslich |
| 5,562,736 | A | 10/1996 | Ray et al. |
| 5,571,109 | A | 11/1996 | Bertagnoli |
| 5,571,189 | A | 11/1996 | Kuslich |
| 5,571,190 | A | 11/1996 | Ulrich et al. |
| 5,575,790 | A | 11/1996 | Chen et al. |
| 5,593,409 | A | 1/1997 | Michelson |
| 5,601,556 | A | 2/1997 | Pisharodi |
| 5,601,572 | A | 2/1997 | Middleman et al. |
| 5,632,746 | A | 5/1997 | Middleman et al. |
| 5,645,597 | A | 7/1997 | Krapiva |
| 5,665,122 | A | 9/1997 | Kambin |
| 5,669,926 | A | 9/1997 | Aust et al. |
| 5,674,295 | A | 10/1997 | Ray et al. |
| 5,681,263 | A | 10/1997 | Flesch |
| 5,693,100 | A | 12/1997 | Pisharodi |
| 5,695,513 | A | 12/1997 | Johnson et al. |
| 5,700,239 | A | 12/1997 | Yoon |
| 5,702,453 | A | 12/1997 | Rabbe et al. |
| 5,702,454 | A | 12/1997 | Baumgartner |
| 5,716,416 | A | 2/1998 | Lin |
| 5,741,253 | A | 4/1998 | Michelson |
| 5,749,879 | A | 5/1998 | Middleman et al. |
| 5,755,797 | A | 5/1998 | Baumgartner |
| 5,756,127 | A | 5/1998 | Grisoni et al. |
| 5,772,661 | A | 6/1998 | Michelson |
| 5,782,832 | A | 7/1998 | Larsen et al. |
| 5,788,703 | A | 8/1998 | Mittelmeier et al. |
| 5,807,275 | A | 9/1998 | Jamshidi |
| 5,820,628 | A | 10/1998 | Middleman et al. |
| 5,823,979 | A | 10/1998 | Mezo |
| 5,824,093 | A | 10/1998 | Ray et al. |
| 5,827,289 | A | 10/1998 | Reiley et al. |
| 5,836,948 | A | 11/1998 | Zucherman et al. |
| 5,848,986 | A | 12/1998 | Lundquist et al. |
| 5,851,212 | A | 12/1998 | Zirps et al. |
| 5,860,977 | A | 1/1999 | Zucherman et al. |
| 5,865,848 | A | 2/1999 | Baker |
| 5,904,690 | A | 5/1999 | Middleman et al. |
| 5,919,235 | A | 7/1999 | Husson et al. |
| 5,925,074 | A | 7/1999 | Gingras et al. |
| 5,961,554 | A | 10/1999 | Janson et al. |
| 5,972,015 | A | 10/1999 | Scribner et al. |
| 5,976,186 | A | 11/1999 | Bao et al. |
| 5,980,522 | A | 11/1999 | Koros et al. |
| 6,012,494 | A | 1/2000 | Balazs |
| 6,015,436 | A | 1/2000 | Schonhoffer |

| Patent | Type | Date | Inventor |
|---|---|---|---|
| 6,019,793 | A | 2/2000 | Perren et al. |
| 6,030,401 | A | 2/2000 | Marino |
| 6,033,406 | A | 3/2000 | Mathews |
| 6,033,412 | A | 3/2000 | Losken et al. |
| 6,039,740 | A | 3/2000 | Olerud |
| 6,045,552 | A | 4/2000 | Zucherman et al. |
| 6,048,342 | A | 4/2000 | Zucherman et al. |
| 6,048,346 | A | 4/2000 | Reiley et al. |
| 6,048,360 | A | 4/2000 | Khosravi et al. |
| 6,066,154 | A | 5/2000 | Reiley et al. |
| 6,068,630 | A | 5/2000 | Zucherman et al. |
| 6,073,051 | A | 6/2000 | Sharkey et al. |
| 6,083,225 | A | 7/2000 | Winslow et al. |
| 6,090,143 | A | 7/2000 | Meriwether et al. |
| 6,102,950 | A | 8/2000 | Vaccaro |
| 6,110,210 | A | 8/2000 | Norton et al. |
| 6,113,640 | A | 9/2000 | Tormala et al. |
| 6,119,044 | A | 9/2000 | Kuzma |
| 6,123,705 | A | 9/2000 | Michelson |
| 6,126,660 | A | 10/2000 | Dietz |
| 6,127,597 | A | 10/2000 | Beyar et al. |
| 6,159,211 | A | 12/2000 | Boriani et al. |
| 6,159,244 | A | 12/2000 | Suddaby |
| 6,165,218 | A | 12/2000 | Husson et al. |
| 6,174,337 | B1 | 1/2001 | Keenan |
| 6,179,873 | B1 | 1/2001 | Zientek |
| 6,187,048 | B1 | 2/2001 | Milner et al. |
| 6,190,414 | B1 | 2/2001 | Young et al. |
| 6,193,757 | B1 | 2/2001 | Foley et al. |
| 6,197,033 | B1 | 3/2001 | Haid, Jr. et al. |
| D439,980 | S | 4/2001 | Reiley et al. |
| 6,217,579 | B1 | 4/2001 | Koros |
| 6,221,082 | B1 | 4/2001 | Marino et al. |
| 6,224,603 | B1 | 5/2001 | Marino |
| 6,235,030 | B1 | 5/2001 | Zucherman et al. |
| 6,235,043 | B1 | 5/2001 | Reiley et al. |
| 6,238,491 | B1 | 5/2001 | Davidson et al. |
| 6,241,734 | B1 | 6/2001 | Scribner et al. |
| 6,248,110 | B1 | 6/2001 | Reiley et al. |
| 6,251,140 | B1 | 6/2001 | Marino et al. |
| 6,261,289 | B1 | 7/2001 | Levy |
| 6,264,695 | B1 | 7/2001 | Stoy |
| 6,267,763 | B1 | 7/2001 | Castro |
| 6,280,456 | B1 | 8/2001 | Scribner et al. |
| 6,280,475 | B1 | 8/2001 | Bao et al. |
| 6,290,724 | B1 | 9/2001 | Marino |
| D449,691 | S | 10/2001 | Reiley et al. |
| 6,296,647 | B1 | 10/2001 | Robioneck et al. |
| 6,312,443 | B1 | 11/2001 | Stone |
| 6,364,828 | B1 | 4/2002 | Yeung et al. |
| 6,368,325 | B1 | 4/2002 | McKinley et al. |
| 6,387,130 | B1 | 5/2002 | Stone et al. |
| 6,402,750 | B1 | 6/2002 | Atkinson et al. |
| 6,419,641 | B1 | 7/2002 | Mark et al. |
| 6,419,705 | B1 | 7/2002 | Erickson |
| 6,423,071 | B1 | 7/2002 | Lawson |
| 6,423,083 | B2 | 7/2002 | Reiley et al. |
| 6,423,089 | B1 | 7/2002 | Gingras et al. |
| 6,425,887 | B1 | 7/2002 | McGuckin et al. |
| 6,425,919 | B1 | 7/2002 | Lambrecht |
| 6,428,541 | B1 | 8/2002 | Boyd et al. |
| 6,436,140 | B1 | 8/2002 | Liu et al. |
| 6,440,138 | B1 | 8/2002 | Reiley et al. |
| 6,451,019 | B1 | 9/2002 | Zucherman et al. |
| 6,468,279 | B1 | 10/2002 | Reo |
| 6,478,805 | B1 | 11/2002 | Marino et al. |
| 6,482,235 | B1 | 11/2002 | Lambrecht et al. |
| 6,485,518 | B1 | 11/2002 | Cornwall et al. |
| D467,657 | S | 12/2002 | Scribner |
| 6,488,710 | B2 | 12/2002 | Besselink |
| 6,491,626 | B1 | 12/2002 | Stone et al. |
| 6,491,695 | B1 | 12/2002 | Roggenbuck |
| 6,498,421 | B1 | 12/2002 | Oh et al. |
| 6,500,178 | B2 | 12/2002 | Zucherman et al. |
| 6,500,205 | B1 | 12/2002 | Michelson |
| 6,508,839 | B1 | 1/2003 | Lambrecht et al. |
| 6,511,471 | B2 | 1/2003 | Rosenman et al. |
| 6,512,958 | B1 | 1/2003 | Swoyer et al. |
| D469,871 | S | 2/2003 | Sand |
| 6,520,991 | B2 | 2/2003 | Huene |
| D472,323 | S | 3/2003 | Sand |
| 6,530,930 | B1 | 3/2003 | Marino et al. |
| 6,533,791 | B1 | 3/2003 | Betz et al. |
| 6,533,797 | B1 | 3/2003 | Stone et al. |
| 6,540,747 | B1 | 4/2003 | Marino |
| 6,554,833 | B2 | 4/2003 | Levy et al. |
| 6,558,390 | B2 | 5/2003 | Cragg |
| 6,562,074 | B2 | 5/2003 | Gerbec et al. |
| 6,575,919 | B1 | 6/2003 | Reiley et al. |
| 6,575,979 | B1 | 6/2003 | Cragg |
| 6,576,016 | B1 | 6/2003 | Hochshuler et al. |
| 6,579,291 | B1 | 6/2003 | Keith et al. |
| 6,582,431 | B1 | 6/2003 | Ray |
| 6,582,433 | B2 | 6/2003 | Yun |
| 6,595,998 | B2 | 7/2003 | Johnson et al. |
| 6,602,293 | B1 | 8/2003 | Biermann et al. |
| 6,607,530 | B1 | 8/2003 | Carl et al. |
| 6,607,544 | B1 | 8/2003 | Boucher et al. |
| 6,610,094 | B2 | 8/2003 | Husson |
| 6,613,054 | B2 | 9/2003 | Scribner et al. |
| 6,620,196 | B1 | 9/2003 | Trieu |
| 6,623,505 | B2 | 9/2003 | Scribner et al. |
| D482,787 | S | 11/2003 | Reiss |
| 6,641,587 | B2 | 11/2003 | Scribner et al. |
| 6,645,213 | B2 | 11/2003 | Sand et al. |
| 6,648,917 | B2 | 11/2003 | Gerbec et al. |
| D483,495 | S | 12/2003 | Sand |
| 6,656,178 | B1 | 12/2003 | Veldhuizen et al. |
| 6,656,180 | B2 | 12/2003 | Stahurski |
| 6,660,037 | B1 | 12/2003 | Husson et al. |
| 6,663,647 | B2 | 12/2003 | Reiley et al. |
| 6,666,890 | B2 | 12/2003 | Michelson |
| 6,666,891 | B2 | 12/2003 | Boehm, Jr. et al. |
| 6,676,663 | B2 | 1/2004 | Higueras et al. |
| 6,676,665 | B2 | 1/2004 | Foley et al. |
| 6,682,561 | B2 | 1/2004 | Songer et al. |
| 6,685,742 | B1 | 2/2004 | Jackson |
| 6,689,125 | B1 | 2/2004 | Keith et al. |
| 6,689,168 | B2 | 2/2004 | Lieberman |
| 6,692,563 | B2 | 2/2004 | Zimmermann |
| 6,706,070 | B1 | 3/2004 | Wagner et al. |
| 6,716,216 | B1 | 4/2004 | Boucher et al. |
| 6,716,247 | B2 | 4/2004 | Michelson |
| 6,716,957 | B2 | 4/2004 | Tunc |
| 6,719,761 | B1 | 4/2004 | Reiley et al. |
| 6,719,773 | B1 | 4/2004 | Boucher et al. |
| 6,723,128 | B2 | 4/2004 | Uk |
| 6,726,691 | B2 | 4/2004 | Osorio et al. |
| D490,159 | S | 5/2004 | Sand |
| 6,740,093 | B2 | 5/2004 | Hochshuler et al. |
| D492,032 | S | 6/2004 | Muller et al. |
| 6,749,560 | B1 | 6/2004 | Konstorum et al. |
| 6,755,841 | B2 | 6/2004 | Fraser et al. |
| D492,775 | S | 7/2004 | Doelling et al. |
| D493,533 | S | 7/2004 | Blain |
| 6,758,673 | B2 | 7/2004 | Fromovich et al. |
| 6,764,514 | B1 | 7/2004 | Li et al. |
| D495,417 | S | 8/2004 | Doelling et al. |
| 6,773,460 | B2 | 8/2004 | Jackson |
| 6,780,151 | B2 | 8/2004 | Grabover et al. |
| 6,783,530 | B1 | 8/2004 | Levy |
| 6,793,679 | B2 | 9/2004 | Michelson |
| 6,796,983 | B1 | 9/2004 | Zucherman et al. |
| 6,805,695 | B2 | 10/2004 | Keith et al. |
| 6,805,697 | B1 | 10/2004 | Helm et al. |
| 6,808,537 | B2 | 10/2004 | Michelson |
| 6,814,736 | B2 | 11/2004 | Reiley et al. |
| 6,814,756 | B1 | 11/2004 | Michelson |
| 6,821,298 | B1 | 11/2004 | Jackson |
| 6,830,589 | B2 | 12/2004 | Erickson |
| 6,835,205 | B2 | 12/2004 | Atkinson et al. |
| 6,835,206 | B2 | 12/2004 | Jackson |
| 6,840,944 | B2 | 1/2005 | Suddaby |
| 6,852,126 | B2 | 2/2005 | Ahlgren |
| 6,852,129 | B2 | 2/2005 | Gerbec et al. |
| 6,863,668 | B2 | 3/2005 | Gillespie et al. |
| 6,863,672 | B2 | 3/2005 | Reiley et al. |
| 6,863,673 | B2 | 3/2005 | Gerbec et al. |

| Patent No. | Date | Inventor |
|---|---|---|
| 6,866,682 B1 | 3/2005 | An et al. |
| 6,881,228 B2 | 4/2005 | Zdeblick et al. |
| 6,883,520 B2 | 4/2005 | Lambrecht et al. |
| 6,887,248 B2 | 5/2005 | McKinley et al. |
| 6,893,466 B2 | 5/2005 | Trieu |
| 6,899,716 B2 | 5/2005 | Cragg |
| 6,899,719 B2 | 5/2005 | Reiley et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,945,973 B2 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Reiley et al. |
| 7,048,694 B2 | 5/2006 | Mark et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,383,639 B2 | 6/2008 | Malandain |
| 7,485,134 B2 | 2/2009 | Simonson |
| 7,608,083 B2 | 10/2009 | Lee et al. |
| 7,637,905 B2 | 12/2009 | Saadat et al. |
| 7,828,807 B2 | 11/2010 | LeHuec et al. |
| 8,057,544 B2 | 11/2011 | Schaller |
| 8,187,327 B2 | 5/2012 | Edidin et al. |
| 8,236,029 B2 | 8/2012 | Siegal |
| 2001/0011174 A1 | 8/2001 | Reiley et al. |
| 2001/0016741 A1 | 8/2001 | Burkus et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0045942 A1 | 4/2002 | Ham |
| 2002/0068974 A1 | 6/2002 | Kuslich et al. |
| 2002/0077700 A1 | 6/2002 | Varga et al. |
| 2002/0082584 A1 | 6/2002 | Rosenman et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0191487 A1 | 12/2002 | Sand |
| 2003/0018390 A1 | 1/2003 | Husson |
| 2003/0032963 A1 | 2/2003 | Reiss et al. |
| 2003/0050644 A1 | 3/2003 | Boucher et al. |
| 2003/0069593 A1 | 4/2003 | Tremulis et al. |
| 2003/0074075 A1 | 4/2003 | Thomas, Jr. et al. |
| 2003/0108588 A1 | 6/2003 | Chen et al. |
| 2003/0130664 A1* | 7/2003 | Boucher et al. .......... 606/86 |
| 2003/0171812 A1 | 9/2003 | Grunberg et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0208136 A1 | 11/2003 | Mark et al. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034343 A1 | 2/2004 | Gillespie et al. |
| 2004/0034429 A1 | 2/2004 | Lambrecht et al. |
| 2004/0049203 A1 | 3/2004 | Scribner et al. |
| 2004/0059333 A1 | 3/2004 | Carl et al. |
| 2004/0059339 A1 | 3/2004 | Roehm, III et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0082953 A1 | 4/2004 | Petit |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0098131 A1 | 5/2004 | Bryan et al. |
| 2004/0102774 A1 | 5/2004 | Trieu |
| 2004/0106940 A1 | 6/2004 | Shaolian et al. |
| 2004/0111161 A1 | 6/2004 | Trieu |

| | | | | | |
|---|---|---|---|---|---|
| 2004/0117019 A1 | 6/2004 | Trieu et al. | 2005/0143827 A1 | 6/2005 | Globerman et al. |
| 2004/0133124 A1 | 7/2004 | Bates et al. | 2005/0149022 A1 | 7/2005 | Shaolian et al. |
| 2004/0133229 A1 | 7/2004 | Lambrecht et al. | 2005/0149191 A1 | 7/2005 | Cragg et al. |
| 2004/0133280 A1 | 7/2004 | Trieu | 2005/0149194 A1 | 7/2005 | Ahlgren |
| 2004/0138748 A1 | 7/2004 | Boyer, II et al. | 2005/0149197 A1 | 7/2005 | Cauthen |
| 2004/0153064 A1 | 8/2004 | Foley et al. | 2005/0154396 A1 | 7/2005 | Foley et al. |
| 2004/0153115 A1 | 8/2004 | Reiley et al. | 2005/0154463 A1 | 7/2005 | Trieu |
| 2004/0158206 A1 | 8/2004 | Aboul-Hosn et al. | 2005/0165406 A1 | 7/2005 | Assell et al. |
| 2004/0167561 A1 | 8/2004 | Boucher et al. | 2005/0171539 A1 | 8/2005 | Braun et al. |
| 2004/0167562 A1 | 8/2004 | Osorio et al. | 2005/0171552 A1 | 8/2005 | Johnson et al. |
| 2004/0167625 A1 | 8/2004 | Beyar et al. | 2005/0182412 A1 | 8/2005 | Johnson et al. |
| 2004/0176775 A1 | 9/2004 | Burkus et al. | 2005/0182413 A1 | 8/2005 | Johnson et al. |
| 2004/0186471 A1 | 9/2004 | Trieu | 2005/0182414 A1 | 8/2005 | Manzi et al. |
| 2004/0186528 A1 | 9/2004 | Ries et al. | 2005/0187556 A1 | 8/2005 | Stack et al. |
| 2004/0186573 A1 | 9/2004 | Ferree | 2005/0187558 A1 | 8/2005 | Johnson et al. |
| 2004/0210231 A1 | 10/2004 | Boucher et al. | 2005/0187559 A1 | 8/2005 | Raymond et al. |
| 2004/0210310 A1 | 10/2004 | Trieu | 2005/0187564 A1 | 8/2005 | Jayaraman |
| 2004/0215344 A1 | 10/2004 | Hochschuler et al. | 2005/0197707 A1 | 9/2005 | Trieu et al. |
| 2004/0220580 A1 | 11/2004 | Johnson et al. | 2005/0216018 A1 | 9/2005 | Sennett |
| 2004/0220672 A1 | 11/2004 | Shadduck | 2005/0216087 A1 | 9/2005 | Zucherman et al. |
| 2004/0225296 A1 | 11/2004 | Reiss et al. | 2005/0222684 A1 | 10/2005 | Ferree |
| 2004/0225361 A1 | 11/2004 | Glenn et al. | 2005/0228383 A1 | 10/2005 | Zucherman et al. |
| 2004/0230191 A1 | 11/2004 | Frey et al. | 2005/0228391 A1 | 10/2005 | Levy et al. |
| 2004/0230309 A1 | 11/2004 | DiMauro et al. | 2005/0228397 A1 | 10/2005 | Malandain et al. |
| 2004/0243229 A1 | 12/2004 | Vidlund et al. | 2005/0234425 A1 | 10/2005 | Miller et al. |
| 2004/0249377 A1 | 12/2004 | Kaes et al. | 2005/0234451 A1 | 10/2005 | Markworth |
| 2004/0254520 A1 | 12/2004 | Porteous et al. | 2005/0234452 A1 | 10/2005 | Malandain |
| 2004/0254644 A1 | 12/2004 | Taylor | 2005/0234456 A1 | 10/2005 | Malandain |
| 2004/0260300 A1 | 12/2004 | Gorensek et al. | 2005/0240182 A1 | 10/2005 | Zucherman et al. |
| 2004/0260397 A1 | 12/2004 | Lambrecht et al. | 2005/0240189 A1 | 10/2005 | Rousseau et al. |
| 2004/0267271 A9 | 12/2004 | Scribner et al. | 2005/0240193 A1 | 10/2005 | Layne et al. |
| 2005/0004578 A1 | 1/2005 | Lambrecht et al. | 2005/0240269 A1 | 10/2005 | Lambrecht et al. |
| 2005/0010293 A1 | 1/2005 | Zucherman et al. | 2005/0251149 A1 | 11/2005 | Wenz |
| 2005/0010298 A1 | 1/2005 | Zucherman et al. | 2005/0251260 A1 | 11/2005 | Gerber et al. |
| 2005/0015148 A1 | 1/2005 | Jansen et al. | 2005/0261684 A1 | 11/2005 | Shaolian et al. |
| 2005/0015152 A1 | 1/2005 | Sweeney | 2005/0261695 A1 | 11/2005 | Cragg et al. |
| 2005/0033295 A1 | 2/2005 | Wisnewski | 2005/0261781 A1 | 11/2005 | Sennett et al. |
| 2005/0033440 A1 | 2/2005 | Lambrecht et al. | 2005/0273166 A1 | 12/2005 | Sweeney |
| 2005/0038517 A1 | 2/2005 | Carrison et al. | 2005/0273173 A1 | 12/2005 | Gordon |
| 2005/0043737 A1 | 2/2005 | Reiley et al. | 2005/0278023 A1 | 12/2005 | Zwirkoski |
| 2005/0043796 A1 | 2/2005 | Grant et al. | 2005/0278027 A1 | 12/2005 | Hyde, Jr. |
| 2005/0055097 A1 | 3/2005 | Grunberg et al. | 2005/0278029 A1 | 12/2005 | Trieu |
| 2005/0060036 A1 | 3/2005 | Schultz et al. | 2005/0283244 A1 | 12/2005 | Gordon et al. |
| 2005/0060038 A1 | 3/2005 | Lambrecht et al. | 2005/0287071 A1 | 12/2005 | Wenz |
| 2005/0065519 A1 | 3/2005 | Michelson | 2006/0004456 A1 | 1/2006 | McKay |
| 2005/0065609 A1 | 3/2005 | Wardlaw | 2006/0009779 A1 | 1/2006 | Collins et al. |
| 2005/0069571 A1 | 3/2005 | Slivka et al. | 2006/0030850 A1 | 2/2006 | Keegan et al. |
| 2005/0070908 A1 | 3/2005 | Cragg | 2006/0030943 A1 | 2/2006 | Peterman |
| 2005/0070911 A1 | 3/2005 | Carrison et al. | 2006/0036241 A1 | 2/2006 | Siegal |
| 2005/0070913 A1 | 3/2005 | Milbocker et al. | 2006/0036259 A1 | 2/2006 | Carl et al. |
| 2005/0071011 A1 | 3/2005 | Ralph et al. | 2006/0036261 A1 | 2/2006 | McDonnell |
| 2005/0080488 A1 | 4/2005 | Schultz | 2006/0036273 A1 | 2/2006 | Siegal |
| 2005/0085912 A1 | 4/2005 | Arnin et al. | 2006/0058807 A1 | 3/2006 | Landry et al. |
| 2005/0090833 A1 | 4/2005 | DiPoto | 2006/0058880 A1 | 3/2006 | Wysocki et al. |
| 2005/0090852 A1 | 4/2005 | Layne et al. | 2006/0064171 A1 | 3/2006 | Trieu |
| 2005/0090899 A1 | 4/2005 | DiPoto | 2006/0069439 A1 | 3/2006 | Zucherman et al. |
| 2005/0107880 A1 | 5/2005 | Shimp et al. | 2006/0069440 A1 | 3/2006 | Zucherman et al. |
| 2005/0113918 A1 | 5/2005 | Messerli et al. | 2006/0085002 A1 | 4/2006 | Trieu et al. |
| 2005/0113919 A1 | 5/2005 | Cragg et al. | 2006/0085009 A1 | 4/2006 | Truckai et al. |
| 2005/0113928 A1 | 5/2005 | Cragg et al. | 2006/0089642 A1 | 4/2006 | Diaz et al. |
| 2005/0118228 A1 | 6/2005 | Trieu | 2006/0089646 A1 | 4/2006 | Bonutti |
| 2005/0119662 A1 | 6/2005 | Reiley et al. | 2006/0089654 A1 | 4/2006 | Lins et al. |
| 2005/0119750 A1 | 6/2005 | Studer | 2006/0089715 A1 | 4/2006 | Truckai et al. |
| 2005/0119751 A1 | 6/2005 | Lawson | 2006/0089718 A1 | 4/2006 | Zucherman et al. |
| 2005/0119752 A1 | 6/2005 | Williams et al. | 2006/0089719 A1 | 4/2006 | Trieu |
| 2005/0119754 A1 | 6/2005 | Trieu et al. | 2006/0095045 A1 | 5/2006 | Trieu |
| 2005/0124989 A1 | 6/2005 | Suddaby | 2006/0095046 A1 | 5/2006 | Trieu et al. |
| 2005/0124992 A1 | 6/2005 | Ferree | 2006/0095134 A1 | 5/2006 | Trieu et al. |
| 2005/0124999 A1 | 6/2005 | Teitelbaum et al. | 2006/0095138 A1 | 5/2006 | Truckai et al. |
| 2005/0125066 A1 | 6/2005 | McAfee | 2006/0100706 A1 | 5/2006 | Shadduck et al. |
| 2005/0131267 A1 | 6/2005 | Talmadge | 2006/0106397 A1 | 5/2006 | Lins |
| 2005/0131268 A1 | 6/2005 | Talmadge | 2006/0106459 A1 | 5/2006 | Truckai et al. |
| 2005/0131269 A1 | 6/2005 | Talmadge | 2006/0122704 A1 | 6/2006 | Vresilovic et al. |
| 2005/0131536 A1 | 6/2005 | Eisermann et al. | 2006/0129244 A1 | 6/2006 | Ensign |
| 2005/0131540 A1 | 6/2005 | Trieu | 2006/0136064 A1 | 6/2006 | Sherman |
| 2005/0131541 A1 | 6/2005 | Trieu | 2006/0142858 A1 | 6/2006 | Colleran et al. |
| 2005/0137602 A1 | 6/2005 | Assell et al. | 2006/0142864 A1 | 6/2006 | Cauthen |
| 2005/0142211 A1 | 6/2005 | Wenz | 2006/0149136 A1 | 7/2006 | Seto et al. |
| 2005/0143763 A1 | 6/2005 | Ortiz et al. | 2006/0149237 A1 | 7/2006 | Markworth et al. |

| | | |
|---|---|---|
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0155379 A1 | 7/2006 | Heneveld, Jr. et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen, III et al. |
| 2006/0173545 A1 | 8/2006 | Cauthen, III et al. |
| 2006/0178746 A1 | 8/2006 | Bartish, Jr. et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195191 A1 | 8/2006 | Sweeney, II et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow |
| 2006/0276899 A1 | 12/2006 | Zipnick et al. |
| 2006/0282167 A1 | 12/2006 | Lambrecht et al. |
| 2006/0287726 A1 | 12/2006 | Segal et al. |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0123986 A1 | 5/2007 | Schaller |
| 2007/0135922 A1 | 6/2007 | Trieu |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0179612 A1 | 8/2007 | Johnson et al. |
| 2007/0179615 A1 | 8/2007 | Heinz et al. |
| 2007/0179616 A1 | 8/2007 | Braddock, Jr. et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0051897 A1 | 2/2008 | Lopez et al. |
| 2008/0071356 A1 | 3/2008 | Greenhalgh et al. |
| 2008/0097611 A1 | 4/2008 | Mastrorio et al. |
| 2008/0125865 A1 | 5/2008 | Abdelgany |
| 2008/0140207 A1 | 6/2008 | Olmos et al. |
| 2008/0167657 A1 | 7/2008 | Greenhalgh |
| 2008/0177306 A1 | 7/2008 | Lamborne et al. |
| 2008/0195210 A1 | 8/2008 | Milijasevic et al. |
| 2008/0221687 A1 | 9/2008 | Viker |
| 2008/0229597 A1 | 9/2008 | Malandain |
| 2008/0243251 A1 | 10/2008 | Stad et al. |
| 2008/0281346 A1 | 11/2008 | Greenhalgh et al. |
| 2008/0281364 A1 | 11/2008 | Chirico et al. |
| 2009/0018524 A1 | 1/2009 | Greenhalgh et al. |
| 2009/0030423 A1 | 1/2009 | Puno |
| 2009/0048678 A1 | 2/2009 | Saal et al. |

FOREIGN PATENT DOCUMENTS

| | | |
|---|---|---|
| DE | 202006005868 | 6/2006 |
| EP | 0529275 A2 | 3/1993 |
| EP | 0 621 020 A1 | 10/1994 |
| EP | 1 157 676 A1 | 4/2001 |
| EP | 1157676 A1 | 11/2001 |
| FR | 2712486 A1 | 5/1995 |
| FR | 2 913 331 | 12/2008 |
| WO | WO 93/04634 | 3/1993 |
| WO | WO 00/67650 | 11/2000 |
| WO | WO 00/67651 | 11/2000 |
| WO | WO 01/10316 A1 | 2/2001 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |

| | | |
|---|---|---|
| WO | WO 03/007854 A1 | 1/2003 |
| WO | WO 03/020169 A2 | 3/2003 |
| WO | WO 03/022165 A1 | 3/2003 |
| WO | WO 03/028587 A2 | 4/2003 |
| WO | WO 03/059180 A2 | 7/2003 |
| WO | WO 03/101308 A1 | 12/2003 |
| WO | WO2004/034924 A2 | 4/2004 |
| WO | WO 2004034924 A2 * | 4/2004 |
| WO | WO 2004/062505 A1 | 7/2004 |
| WO | WO 2004/082526 A2 | 9/2004 |
| WO | WO 2004/098420 A2 | 11/2004 |
| WO | WO 2004/108022 A1 | 12/2004 |
| WO | WO 2005/032433 A2 | 4/2005 |
| WO | WO 2005/051246 A2 | 6/2005 |
| WO | WO 2005/081877 A2 | 9/2005 |
| WO | WO 2006/047645 A2 | 5/2006 |
| WO | WO 2006/060420 A1 | 6/2006 |
| WO | WO 2006/066228 A2 | 6/2006 |
| WO | WO 2006/072941 A2 | 7/2006 |
| WO | WO 2007/022194 | 2/2007 |
| WO | WO2007/067726 A2 | 6/2007 |

OTHER PUBLICATIONS

USPTO Supplemental Notice of Allowability of Dec. 31, 2009 for U.S. Appl. No. 11/464,790.
USPTO Notice of Allowance and Fee(s) Due of Dec. 23, 2009 for U.S. Appl. No. 11/464,793.
UPSTO Supplemental Notice of Allowability of Dec. 31, 2009 for U.S. Appl. No. 11/464,793.
USPTO Notice of Allowance and Fee(s) Due of Dec. 23, 2009 for U.S. Appl. No. 11/464,812.
USPTO Supplemental Notice of Allowability of Dec. 31, 2009 for U.S. Appl. No. 11/464,812.
USPTO Notice of Allowance and Fee(s) Due of Dec. 17, 2009 for U.S. Appl. No. 11/464,815.
USPTO Supplemental Notice of Allowability of Dec. 31, 2009 for U.S. Appl. No. 11/464,815.
John A. Carrino, Roxanne Chan and Alexander R. Vaccaro, "Vertebral Augmentation: Vertebroplasty and Kyphoplasty", Seminars in Roentgenology, vol. 39, No. 1 (January), 2004: pp. 68-84.
Ajeya P. Joshi, M.D. and Paul A. Glazer, M.D., "Vertebroplasty: Current Concepts and Outlook", 2003, (9 Pages), From: http://www.spineuniverse.com/displayarticle.php/article2076.html.
PCT Invitation to Pay Additional Fees (Form PCT/ISA/206), Re: International application No. PCT/US2006/031861 dated Jan. 15, 2007.
Annex to PCT Invitation to Pay Additional Fees, Re: International application No. PCT/US2006/031861 dated Jan. 15, 2007.
PCT Notification concerning transmittal of International Preliminary report on patentability and PCT Written Opinion of the International Searching Authority, PCT Application No. US2006/031861 dated Feb. 28, 2008.
USPTO Office Action of Jun. 23, 2008 for U.S. Appl. No. 11/464,782.
USPTO Office Action of Oct. 29, 2008 for U.S. Appl. No. 11/464,782.
USPTO Office Action of May 21, 2009 for U.S. Appl. No. 11/464,782.
USPTO Office Action of Jun. 23, 2008 for U.S. Appl. No. 11/464,790.
USPTO Office Action of Oct. 31, 2008 for U.S. Appl. No. 11/464,790.
USPTO Office Action of Apr. 15, 2009 for U.S. Appl. No. 11/464,790.
USPTO Office Action of Jun. 23, 2008 for U.S. Appl. No. 11/464,793.
USPTO Office Action of Oct. 29, 2008 for U.S. Appl. No. 11/464,793.
USPTO Office Action of May 22, 2009 for U.S. Appl. No. 11/464,793.
USPTO Office Action of Aug. 19, 2009 for U.S. Appl. No. 11/464,807.
USPTO Office Action of Jun. 23, 2008 for U.S. Appl. No. 11/464,812.
USPTO Office Action of Oct. 29, 2008 for U.S. Appl. No. 11/464,812.
USPTO Office Action of May 12, 2009 for U.S. Appl. No. 11/464,812.
USPTO Office Action of Jun. 23, 2008 for U.S. Appl. No. 11/464,815.
USPTO Office Action of Oct. 29, 2008 for U.S. Appl. No. 11/464,815.
USPTO Office Action of May 12, 2009 for U.S. Appl. No. 11/464,815.
Notification of Transmittal of International Search Report, International Search Report and Written Opinion for PCT/US08/54590 dated Aug. 22, 2008.
Notification of Transmittal of International Search Report, International Search Report and Written Opinion for PCT/US08/54508 dated Aug. 27, 2008.
U.S. Appl. No. 60/689,570, filed Jun. 13, 2005; Inventor: Tzony Siegal; Title: Directional Drilling System.
U.S. Appl. No. 60/557,246, filed Mar. 29, 2004 entitled: Device and Methods to Reduce and Stabilize Broken Bones.
Edeland, H.G., "Some Additional Suggestions for an Intervetebral Disc Prosthesis", J of BioMedical Engr., vol. 7(1) pp. 57-62, Jan. 1985.
Office Action issued in European Patent App. No. 06801545.2 dated May 30, 2011.
Translation of Office Action issued in Japanese Patent App. No. 2008-527067 dated May 13, 2011.
Office Action issued in Australian Patent App. No. 2006279558 dated Aug. 8, 2011.

* cited by examiner

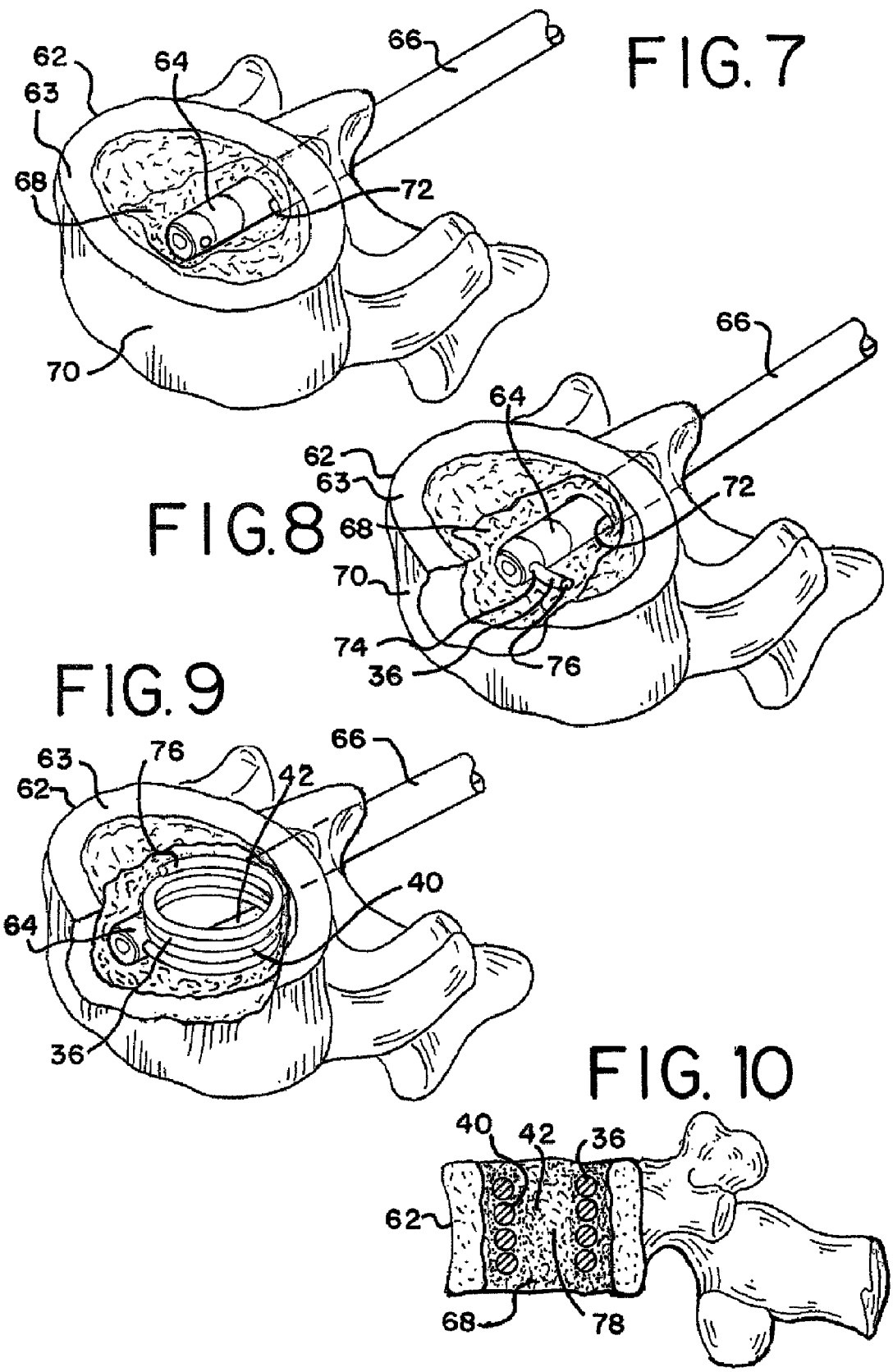

APPARATUS AND METHOD FOR TREATING BONE

The present application is a continuation-in-part of U.S. patent application Ser. No. 11/464,782 now U.S. Pat. No. 7,785,368, a continuation-in-part of U.S. patent application Ser. No. 11/464,790 now U.S. Pat. No. 7,666,226, a continuation-in-part of U.S. patent application Ser. No. 11/464,793 now U.S. Pat. No. 7,666,227, a continuation-in-part of U.S. patent application Ser. No. 11/464,807, a continuation-in-part of U.S. patent application Ser. No. 11/464,812 now U.S. Pat. No. 7,670,374 and a continuation-in-part of U.S. patent application Ser. No. 11/464,815 now U.S. Pat. No. 7,670,375, all of which were filed on Aug. 15, 2006 and claim the benefit of Provisional Patent Application No. 60/708,691, filed Aug. 16, 2005, U.S. Provisional Patent Application No. 60/738,432, filed Nov. 21, 2005 and U.S. Provisional Patent Application No. 60/784,185, filed Mar. 21, 2006, all of the above are incorporated herein by reference. The present patent application also claims the benefit of U.S. Provisional Application No. 60/886,838, filed Jan. 26, 2007, U.S. Provisional Application No. 60/890,868, filed Feb. 21, 2007, and U.S. Provisional Application No. 60/936,974, filed Jun. 22, 2007, all of which are hereby incorporated herein by reference.

FIELD OF INVENTION

The present disclosure generally relates to apparatus and methods for the treatment of bone conditions and, more particularly, to apparatus and methods for forming passageways within bone tissue, such as bone tamps, and interdigitating bone filler material with bone tissue.

BACKGROUND OF INVENTION

Bones or portions of bones often comprise an outer relatively hard layer referred to as cortical bone and inner material referred to as cancellous bone. A variety of physical conditions can cause cancellous bone to become diseased or weakened. Such conditions can include, for example, osteoporosis, avascular necrosis, cancer or trauma. Weakened cancellous bone can result in an increased risk of fracture of the cortical bone surrounding the cancellous bone, because the diseased or weakened cancellous bone provides less support to the exterior cortical bone than healthy cancellous bone.

One common condition that is caused by diseased or damaged cancellous bone is vertebral compression fractures. A vertebral compression fracture is a crushing or collapsing injury to one or more vertebrae. One of the leading causes, but not an exclusive cause, of vertebral compression fractures is osteoporosis. Osteoporosis reduces bone density, thereby weakening bones and predisposing them to fracture. The osteoporosis-weakened vertebrae can collapse during normal activity and are also more vulnerable to injury from shock or other forces acting on the spine. In severe cases of osteoporosis, actions as simple as bending can be enough to cause a vertebral compression fracture.

While the vertebral compression fractures may heal without intervention, the crushed bone may fail to heal adequately. Moreover, if the bones are allowed to heal on their own, the spine may be deformed to the extent the vertebrae were compressed by the fracture. Spinal deformity may lead to other adverse conditions, such as, breathing and gastrointestinal complications, and adverse physical effect on adjacent vertebrae.

Minimally invasive surgical techniques for treating vertebral compression fractures are becoming more and more common. One such technique used to treat vertebral compression fractures is injection of bone filler material into the fractured vertebral body. This procedure is commonly referred to as percutaneous vertebroplasty. More specifically, vertebroplasty involves inserting an inject needle into bone material in the vertebra and injecting bone filler material (for example, bone cement, allograph material or autograph material) into the collapsed vertebra to stabilize and strengthen the crushed bone.

Another type of treatment for vertebral compression fractures is known as Kyphoplasty. Kyphoplasty is a modified vertebroplasty treatment that uses one or two balloons, introduced into the vertebra. First a cannula or other device is inserted into the vertebra. The cannula may have one or more balloons associated with it or another device may be inserted with balloons. As the balloons are inflated, the balloons push the cancellous bone outwardly, crushing or compacting the cancellous bone to create a cavity, which significantly alters the natural structure of the cancellous bone. The balloons are then deflated and removed, leaving a cavity. Bone cement is injected into the cavity to stabilize the fracture.

SUMMARY OF THE INVENTION

The present disclosure relates to apparatus and methods that are employed to treat bone tissue, such as cancellous bone tissue. More particularly, the present disclosure relates to a bone tamp and methods of use thereof that can be employed to create one or more passageway channels within bone tissue for any number of bone treatment procedures. For example, the bone tamp can be employed to created a channel or pathway in cancellous bone tissue of a vertebral body in a vertebroplasty-type procedure.

One aspect of the present disclosure relates to apparatus for forming channels in bone tissue. The apparatus includes an elongated member adapted for being deployed into and withdrawn from bone tissue. The elongated member is deformable from an original or as-made generally non-linear configuration into a modified or ready generally linear configuration for insertion of the elongated member into bone tissue. As the elongated member is inserted into the bone tissue, the elongated member returns or transitions, in one embodiment by self-forming, back into the original or as-made generally non-linear configuration within the bone tissue. The elongated member is also deformable into a generally linear configuration for withdrawal from the bone tissue.

Another aspect of the present invention relates to a method for creating a passageway channel within bone tissue. The method includes providing an elongated member having a generally non-linear configuration and applying an external force to change the shape of the elongated member into a more linear configuration. While in the more-linear configuration, the elongated member is inserted into bone tissue and the external force is removed to allow the elongated member to substantially return to the generally non-linear configuration. After insertion into bone tissue, the elongated member may be withdrawn from the bone tissue to create a passageway or channel within the bone tissue.

A further aspect of the present disclosure relates to a method of interdigitating bone filler material and bone tissue. The method includes providing an elongated member which is constrained in a generally linear configuration, and which member is biased to form a non-linear configuration when the constraint is removed. While in the generally linear configuration, the elongate member is inserted into bone tissue and the constraint is removed from the elongated member to allow the elongated member to assume the generally non-linear configuration within the bone tissue. The elongated member may thereafter be withdrawn from the bone tissue, thereby creating a passageway or channel within the bone tissue. After the channel has been created, bone filler material, such as PMMA, bone paste, bone cement, allograph, autograph or any other suitable flowable material, is injected into the channel to interdigitate the flowable material with the bone tissue.

BRIEF DESCRIPTION OF THE FIGURES

In the course of this description, reference will be made to the accompanying drawings, wherein:

FIG. 7 is top a perspective view of a vertebra having portions broken away to show the distal end of a deployment cannula inserted within the vertebral body;

FIG. 8 is a top perspective view of the vertebra of FIG. 7 having portions broken away to show a bone tamp partially extending out of the distal end of the deployment cannula and deployed within the cancellous bone of the vertebral body;

FIG. 9 is a top perspective view of the vertebra of FIG. 8 having portions broken away to show the bone tamp fully deployed within the cancellous bone of the vertebral body;

FIG. 10 is a cross-sectional view of the vertebra of FIG. 9, showing the bone tamp fully deployed;

DETAILED DESCRIPTION

Although detailed embodiments of the present subject matter are disclosed herein, it is to be understood that the disclosed embodiments are merely exemplary, and the subject matter may be embodied in various forms. Therefore, specific details disclosed herein are not to be interpreted as limiting the subject matter claimed, but merely as examples to illustrate and describe the subject matter and various aspects thereof.

As pointed out earlier, the present disclosure pertains to apparatus and methods for forming passageways or channels in bone tissue and interdigitating bone filler material with bone tissue. The apparatus and methods will be described by way of example, but not limitation, in relation to procedures within the vertebral body. The apparatus and methods may be used to treat bone tissue in other areas of the body as well. Moreover, although the bone tamp described herein will be described by way of example, but not limitation, in conjunction with methods for interdigitating bone filler material, the bone tamp and methods of use thereof also can be used to create passageways or channels in bone tissue for virtually any purpose or procedure where such passageways or channels are desired.

Figure 1:
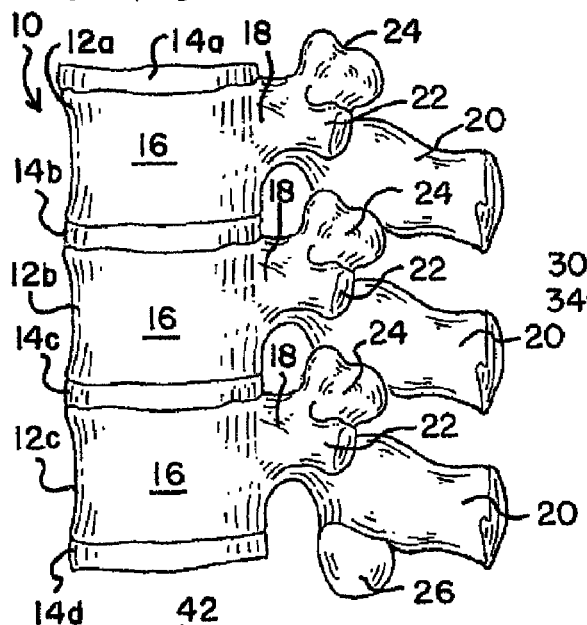
FIG. 1 is a partial side view of a normal human vertebral column.

FIG. 1 illustrates a section of a healthy vertebral (spinal) column, generally designated as 10, free of injury. The vertebral column 10 includes adjacent vertebrae 12a, 12b and 12c and intervertebral disks 14a, 14b, 14c and 14d separating adjacent vertebrae. The vertebrae, generally designated as 12, include a vertebral body 16 that is roughly cylindrically shaped and comprised of spongy inner cancellous bone surrounded by compact bone (referred to as the cortical rim). The body 16 of the vertebra is capped at the top by a superior endplate and at the bottom by an inferior endplate made of a cartilaginous layer. On either side of the vertebral body 16 are the pedicles 18, which lead to the spinal process 20. Other elements of the vertebra include the transverse process 22, the superior articular process 24 and the inferior articular process 26.

In vertebral compression fractures the vertebral body may be fractured from impact (even if healthy) or suffer fractures that result from weakening of the cortical rim such as from osteoporosis. When weakened by osteoporosis, the vertebra is increasingly subject to fracture due to routine forces from standing, bending or lifting.

Figure 2:
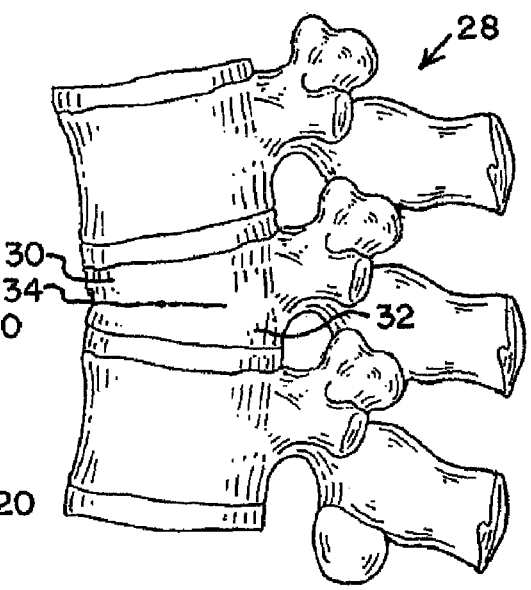
FIG. 2 is comparable to FIG. 1, depicting a vertebral compression fracture in one of the vertebral bodies.

FIG. 2 illustrates a damaged vertebral column, generally designated as 28, with a vertebral body 30 of a vertebra 32 suffering from a compression fracture 34. The vertebral body 30 suffering from the compression fraction 34 becomes typically wedge shaped and reduces the height of both the vertebra 32 and vertebral column 28 on the anterior (or front) side. As a result, this reduction of height can affect the normal curvature of the vertebral column 28. If left untreated, the vertebral body may further collapse and fracture causing additional pain and complications.

Turning now to a detailed description of illustrated embodiments described herein. The apparatus or device of the present disclosure, falls generally into the class of medical devices known as bone tamps osteotome. Bone tamps per se are not new, and the term generally refers to a device with an elongated shaft for insertion into bone. Such bone tamps were known long before the development of vertebroplasty and kyphoplasty. The present subject matter is referred to as a bone tamp because it is inserted into bone tissue, forming a passageway or channel therethrough by reason of its insertion, just as bone tamps have done since their early development.

Figure 3:
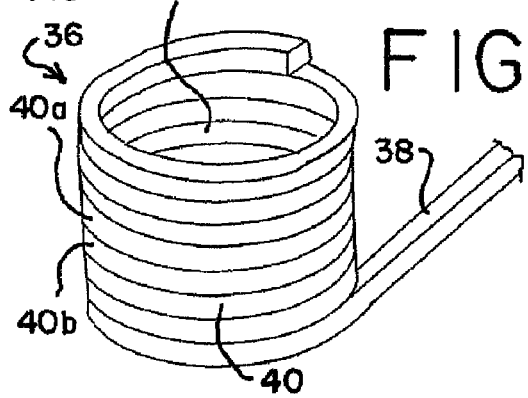
FIG. 3 is a perspective view of one embodiment of a bone tamp of the present disclosure, shown in a helical or coiled configuration.
Figure 4:
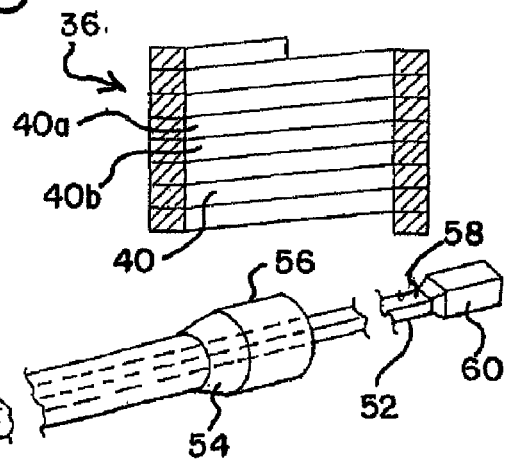
FIG. 4 is a vertical cross-sectional view of the bone tamp of FIG. 3.

FIG. 3 shows a perspective view of one embodiment of the present bone tamp 36 in its initial or original, as-manufactured configuration, and FIG. 4 shows a vertical cross-sectional view of bone tamp 36. In this embodiment, bone tamp 36 is comprised of an elongated member 38, such as a shaft, thread or ribbon, having a rectangular cross-section. In other embodiments, elongated member 38 can have a variety of cross-sectional shapes and profiles, such as round or other simple or complex geometric profiles.

In this initial configuration, bone tamp 36 has a generally helical or coiled configuration. The pitch of the helical configuration can vary depending on the desired application. In other words, the spacing between each winding 40 can vary. In the embodiment shown, the helical configuration has a tight pitch and each turn or winding 40a is wound on top of the previous winding 40b to form a plurality of stacked windings with little or no spacing between each winding. In its initial configuration, bone tamp 36 includes or defines an innerspace or resident volume 42. As used herein, "resident volume" is intended to refer generally to a structural characteristic of bone tamp 36 in its helical configuration in that the bone tamp has a structure that generally defines a resident volume. The resident volume 42 is not necessarily a volume completely enclosed by bone tamp 36 and can be any volume generally defined by the bone tamp. The resident volume is not necessarily empty and can contain material, such as cancellous bone.

Bone tamp 36 can be comprised of any suitable material, but preferably comprises a shape memory material. The shape memory material can be any suitable material, the shape of which can be changed upon application of external force, and which substantially returns to its initial shape upon remove of the external force. Such shape memory materials can include, for example, Nitinol (NiTi) or other suitable alloy (Cu—Al—Ni, Ti—Nb—Al, Au—Cd, etc.) or a shape memory polymer. Bone tamp 36 can be formed into the initial or original helical configuration by any suitable method know in the art, such as the method described in co-owned U.S. patent application Ser. No. 11/464,782, which is incorporated by reference above.

Figure 5:
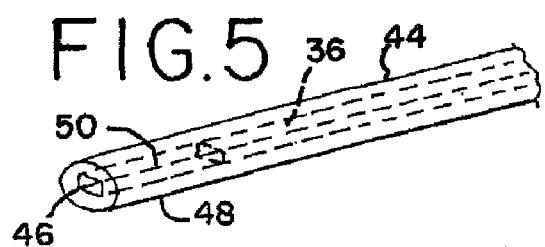
FIG. 5 is a perspective view of a deployment cannula, shown with a bone tamp of the present disclosure in a generally linear configuration within the cannula for deployment.
Figure 6:
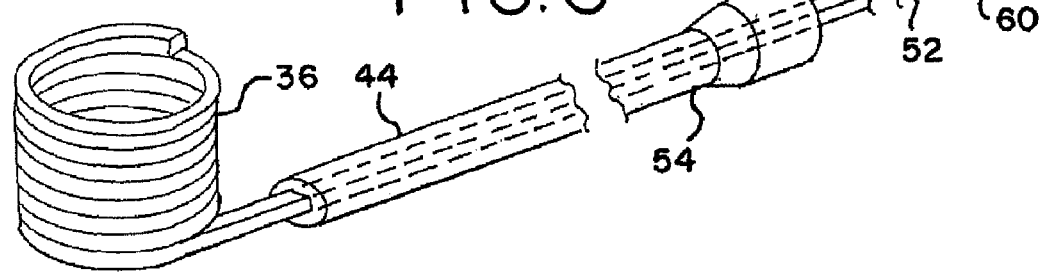
FIG. 6 is a perspective view of the deployment cannula of FIG. 5, shown with the bone tamp partially ejected from the deployment cannula and in a deployed configuration.

FIGS. 5 and 6 are perspective views generally showing the deployment of bone tamp 36 through a deployment cannula 44. Bone tamp 36 is first formed into the initial or original helical or coil shape seen in FIG. 3. Referring to FIG. 5, bone tamp 36 (partially shown in phantom) can be unwound or drawn or forced into a substantially linear or deployment configuration by insertion into a lumen 50 of deployment cannula 44 for delivery. Cannula 44 constrains or otherwise exerts an external force on bone tamp 36 to deform and retain bone tamp 36 in a generally straight configuration as the bone tamp is passed into the cannula. The modified or deployment ready shape of bone tamp 36 is substantially linear, in that the shape can be perfectly straight or the shape could include slight bends or zigzags within the cannula.

Upon exiting opening 46 in a distal end portion 48 of cannula 44, the external force is removed from bone tamp 36 and the bone tamp, by change of configuration, returns to its initial or original shape, or nearly so, as illustrated in FIG. 6. As shown in the partially exited position, a coiled portion of bone tamp 36 is outside of cannula 44 in the original state and the remaining portion of bone tamp 36 is inside the cannula in a modified or ready constrained shape. Bone tamp 36 can be retracted back into cannula 44 and back into the constrained shape as illustrated in FIG. 5 or further ejected from the cannula to assume its original shape.

In one embodiment, opening 46 and lumen 50 of the cannula 44 have a complementary or generally similar cross-sectional shape as bone tamp 36, which aids in deploying the bone tamp in the desired orientation. In the embodiment shown, bone tamp 36 can be advanced or retracted through cannula 44 with the aid of a pushrod 52. Proximal end 54 of cannula 44 may have a knob or handle 56 or other structure for ease of use and proximal end 58 of the pushrod 52 also may have a knob or handle 60 as well. Alternatively, bone tamp 36 can be advanced and retracted through cannula 44 by any suitable drive or gear mechanism.

FIGS. 7-12 illustrate an exemplary method of employing the bone tamp 36 to form a channel within the cancellous bone tissue of a vertebral body. This is, of course, not the only procedure in which the bone tamp may be employed. FIG. 7 is a perspective view of a vertebra 62. As generally described above, vertebral body 70 of vertebra 62 includes cancellous bone tissue 68 surrounded by cortical rim 63. The distal end portion 64 of a deployment cannula 66 is inserted into the cancellous bone 68 of vertebral body 70 through a percutaneous transpedicular access port 72. Portions of vertebra 62 shown in FIGS. 7-9 have been broken way to show the location of the distal end portion of the cannula and the bone tamp within the cancellous bone of the vertebral body.

The transpedicular access port 72 can be made by using standard percutaneous transpedicular techniques that are well known in the art. Typically, such standard techniques include the use of minimally invasive vertebral body access instruments, such as trocars, access needles and working cannulas. If a working cannula is used, the working cannula is inserted into the transpedicular access port 72 and deployment cannula 66 is inserted into the vertebra 62 through the working cannula. Depending on the particular procedure, the deployment cannula can also be inserted into the cancellous bone of the vertebral body through other approaches as well, such as from lateral or anterior approaches.

In the illustrated embodiment, the distal end portion 64 of the deployment cannula 66 is centrally positioned within the vertebral body 70. However, the deployment cannula may be positioned at other locations depending on the desired application. Once deployment cannula 66 is in the desired position within the vertebral body 70, bone tamp 36, in its constrained or generally linear configuration, is advanced through deployment cannula 66 and out of opening 74 in distal end portion 64 of deployment cannula 66, as shown in FIG. 8. In this embodiment, opening 74 comprises an opening in the side of distal end portion 64 of deployment cannula 66.

Upon exiting deployment cannula 66, the external force constraining bone tamp 36 in the generally linear configuration is removed and the bone tamp, due to its shape retention characteristics, begins to substantially revert or self-form into its initial or original helical or coiled shape. Thus, the deployed configuration of bone tamp 36 is substantially the same as its initial or original configuration.

Referring to FIGS. 9 and 10, as bone tamp 36 advances out of the distal end portion 64 of deployment cannula 66, bone tamp 36, due to its mechanical strength and shape retention characteristics, penetrates and transverses through the relatively spongy cancellous bone to create a cylindrical or helically shaped channel or passageway therethrough. In the embodiment shown, the distal end portion 76 of bone tamp 36 has a generally blunted end. In alternative embodiments, distal end portion 76 can have other configurations, such as for example, pointed and sharp surfaces, which aid the bone tamp in penetrating and traversing through the bone tissue.

As shown in FIGS. 9 and 10, the individual loops or windings 40 of bone tamp 36 stack-up one adjacent to the other to create a generally cylindrical structure having a resident volume 42 filled with cancellous bone. Specifically, bone tamp 36 winds through cancellous bone 68 of vertebral body 70 so that undisturbed cancellous bone 78 is located within the resident volume 42. Moreover, depending on the desired application, each winding 40 may be in contact with the adjacent windings or windings 40 may be spaced apart, or bone tamp 36 may contain a combination of touching and spaced apart windings 40.

The deployment of bone tamp 36 can be monitored by fluoroscopic imaging or any other suitable type imaging to help ensure that the bone tamp is forming the desired channel for the particular procedure. Monitoring the deployment of the bone tamp provides several benefits, such as, ensuring the bone tamp is being deployed along the desired path and in the desired orientation.

Figure 11:
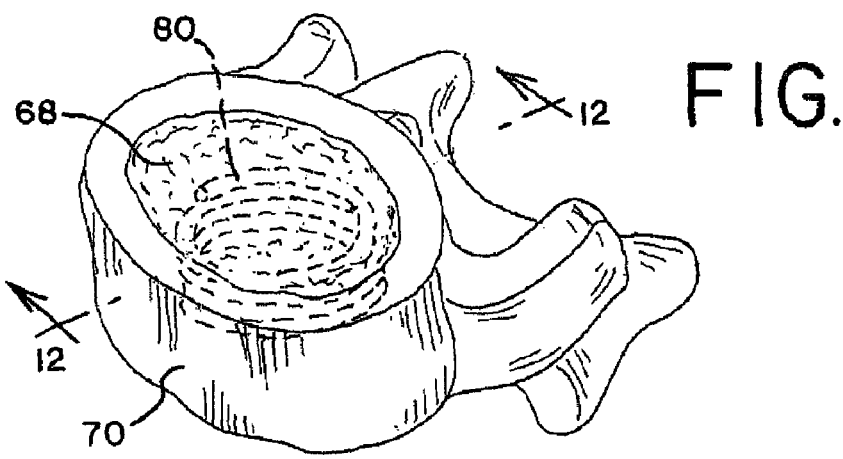
FIG. 11 is a top perspective view of the vertebra of FIG. 9, shown after the bone tamp has been withdrawn from the vertebral body, portions of the vertebral body have been broken away to show the passageway or channel created within the cancellous bone of the vertebral body.
Figure 12:
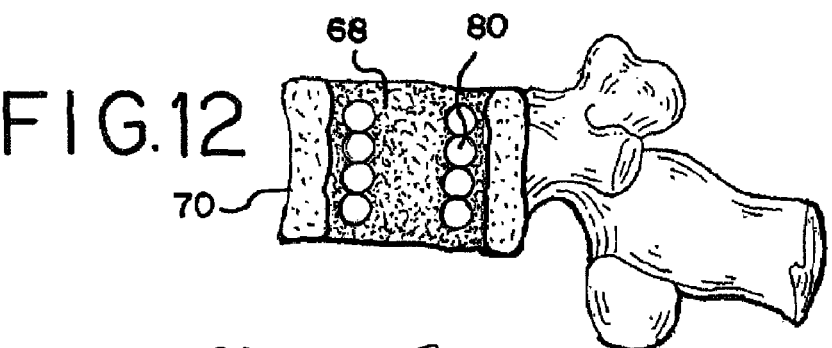
FIG. 12 is a cross-sectional view of the vertebra of FIG. 11.

After the desired portion of bone tamp 36 has been deployed, i.e., a sufficient length of the bone tamp has been deployed to create a channel of the desired size, bone tamp 36 may be retracted from cancellous bone 68 of vertebral body 70 and back into deployment cannula 66. As bone tamp 36 is retracted into the deployment cannula 66, the cannula again applies an external force on the bone tamp and the bone tamp is forced into its generally linear modified or ready configuration. After bone tamp 36 has been fully or substantially retracted into deployment cannula 66, the bone tamp and deployment cannula are withdrawn from the vertebra. As shown in FIGS. 11 and 12, withdrawing bone tamp 36 from the vertebral body 70 leaves a generally cylindrical or helical shaped passageway channel 80 within cancellous bone 68.

As mentioned above, the above described bone tamp and methods of use thereof are not limited to the treatment of vertebral bone tissue and can be used to treat bone tissue in other areas of the body as well. Additionally, the bone tamp can be used in conjunction with a variety of different procedures, such as for example, in a procedure involving interdigitation of bone filler material with bone tissue. One such interdigitation procedure for treating vertebral bodies is illustrated in FIGS. 13 and 14.

Figure 13:
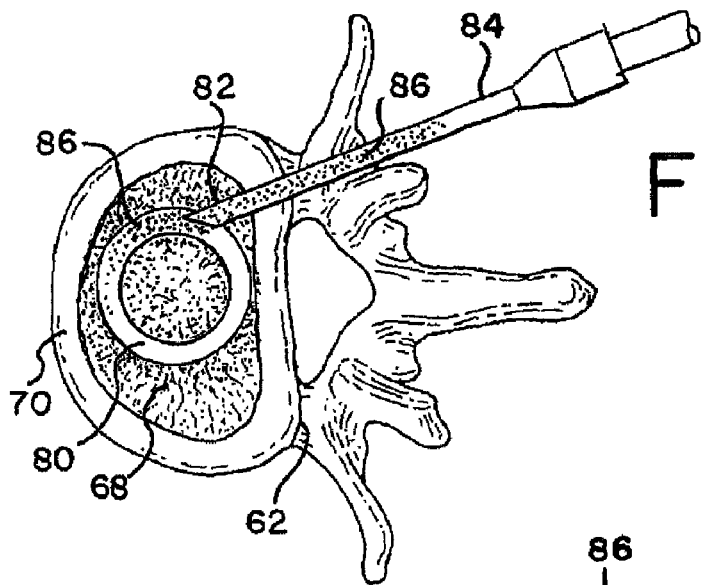
FIG. 13 is a top cross-sectional view of the vertebra of FIG. 11 shown after the channel has been formed and having a bone filler material injection needle inserted into the channel within the cancellous bone.
Figure 14:
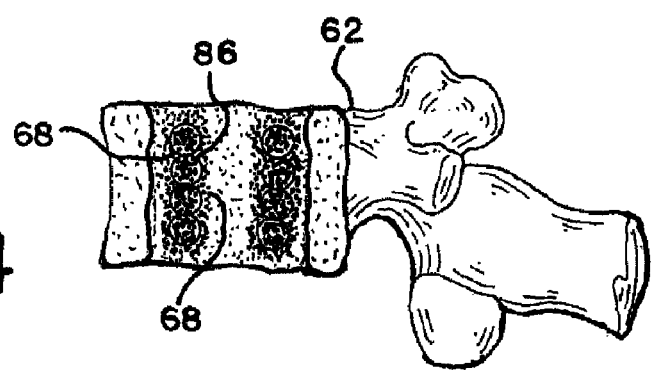
FIG. 14 is a cross-sectional view of the vertebra of FIG. 12 shown with bone filler material within the channel and interdigitating with the cancellous bone.

FIG. 13 illustrates a top cross-sectional view of vertebra 62 after a channel 80 has been created in the cancellous bone 68 of the vertebral body 70 using the bone tamp and methods described herein. After channel 80 has been created in cancellous bone 68, a distal end portion 82 of a bone filler injection needle 84 is inserted into vertebral body 70 to access channel 80. Distal end portion 82 of the bone filler injection needle 84 can be inserted through the same transpedicular access port that was created to insert the bone tamp. Alternatively, distal end portion 82 of the bone filler injection needle 84 can be inserted through a second or different access port, such as a lateral or anterior access port. Moreover, the positioning of distal end portion 82 of the injection needle 84 can be monitored using fluoroscopy to ensure proper positioning of the needle.

Once the injection needle 84 is in the desired position, bone filler material or flowable material 86 may be injected into the channel 80, as shown in FIG. 13. As the bone filler material 86 progresses through the channel 68, the bone filler material also begins to interdigitate with the spongy or porous cancellous bone tissue 68. In other words, the bone filler material migrates or seeps into and through the pores and around the trabeculae of the spongy cancellous bone as illustrated in FIG. 14. A variety of factors contribute to amount of interdigitation and such factors can be controlled by a surgeon to achieve a desired result. Such factors can include, but are not limited to, the size of the channel created in the bone tissue, the viscosity and volume of bone filler material injected, the curing rate of the bone filler material and the amount of injection pressure applied during injection of the bone filler material. After the bone filler material has cured, it is contemplated that it will aid in stabilizing and supporting the cancellous bone and surrounding cortical bone, thereby reducing the risk of collapse or fracture while maintaining the original cancellous bone intact and avoiding the compaction of the bone and creation of a cavity as required in Kyphoplasty.

It will be understood that the embodiments of the present disclosure which have been described are illustrative of some of the applications of the principles of the present invention. Numerous modifications may be made by those skilled in the art without departing from the true spirit and scope of the invention, including those combinations of features that are individually disclosed or claimed herein.

What is claimed is:

1. A bone tamp system for creating channels within bone tissue, comprising:
    an elongated bone tamp for insertion into and withdrawal from bone tissue, the bone tamp having an initial generally curved configuration extending in a generally coiled direction, the bone tamp being deformable into a more generally linear configuration for insertion of the bone tamp into bone tissue, the bone tamp being adapted to transition back into the initial generally curved configuration extending in a generally coiled direction as the bone tamp is inserted into the bone tissue, and the bone tamp being deformable into the more generally linear configuration for withdrawal from the bone tissue, thereby leaving a channel within the bone tissue;
    a bone cement injection device for injecting bone cement into the channel within the bone tissue; and
    an amount of bone cement.

2. The device of claim 1 in which the bone tamp is made of a shape memory material.

3. The device of claim 1 in which the bone tamp is adapted to be inserted into the bone tissue through a cannula.

4. The device of claim 1 in which the generally curved configuration comprises the bone tamp extending in a generally helical direction.

5. The device of claim 1 in which the bone tamp defines a resident volume when in the initial curved configuration.

6. A method of treating bone tissue employing an elongated bone tamp having an initial generally curved configuration extending in a coiled direction, the method comprising:
    applying an external force to change the shape of the bone tamp into a deployment configuration;
    inserting the bone tamp in the deployment configuration into bone tissue;
    removing the external force from the bone tamp as the bone tamp is inserted into the bone tissue, thereby allowing the bone tamp to substantially return to the initial generally curved configuration extending in a generally coiled direction as the bone tamp transverses through bone tissue;
    withdrawing the bone tamp from the bone tissue, thereby leaving a channel within the bone tissue; and
    injecting bone cement into the channel within bone tissue.

7. The method of claim 6 in which the generally curved configuration of the bone tamp comprises extending in a generally helical direction.

8. The method of claim 6 in which the deployment configuration comprises a substantially linear configuration.

9. The method of claim 6 in which the bone tamp comprises a shape memory material.

10. The method of claim 6 in which inserting the bone tamp into bone tissue comprises inserting the bone tamp into bone tissue through a cannula.

11. The method of claim 10 in which applying external force comprises inserting the bone tamp into the cannula and removing the external force comprises extending the bone tamp out of the cannula.

12. The method of claim 11 including extending a desired portion of the bone tamp out of the cannula.

13. The method of claim 6 in which inserting the bone tamp into bone tissue comprises inserting the bone tamp into cancellous bone tissue.

14. The method of claim 6 further comprising traversing the bone tamp through the bone tissue to create a generally helical or cylindrical shaped channel within the bone tissue.

15. A method of interdigitating bone cement and bone tissue employing a bone tamp that is movable between a generally linear configuration when constrained by an external force and a curved configuration extending in a generally coiled direction upon release of the external force, the method comprising:

inserting the bone tamp constrained in the generally linear configuration into bone tissue;

removing the external force from the bone tamp as the bone tamp is inserted through the bone tissue, thereby allowing the bone tamp to substantially transform into a generally curved configuration extending in a generally coiled direction as the bone tamp transverses through the bone tissue;

withdrawing the bone tamp from the bone tissue, thereby leaving a channel within the bone tissue; and injecting bone cement into the channel to interdigitate the bone cement and bone tissue.

16. The method of claim 15 in which inserting the constrained bone tamp comprises inserting the bone tamp into bone tissue through a cannula, wherein the cannula constrains the bone tamp in the generally linear configuration.

17. The method of claim 16 in which removing the external force comprises extending the bone tamp out of the cannula.

18. The method of claim 17 including extending a desired portion of the bone tamp out of the cannula.

19. The method of claim 15 in which the bone tamp extends more than 360 degrees when in the curved configuration.

20. The method of claim 15 in which providing the bone tamp comprises providing a shape memory material.

21. The method of claim 15 in which inserting the bone tamp into bone tissue comprises inserting the bone tamp into cancellous bone tissue.

22. The method of claim 15 further comprising traversing the bone tamp through the bone tissue to create a generally helical or cylindrical shaped channel within the bone tissue.

* * * * *